United States Patent [19]

Semkina et al.

[11] 4,067,792
[45] Jan. 10, 1978

[54] SOLID METAL OXIDE ELECTROLYTE AND METHOD OF MAKING

[76] Inventors: Novella Vladimirovna Semkina, ulitsa Bljukhera, 71/1, kv. 38; Galina Alexandrovna Mamaeva, ulitsa Tekhnologicheskaya, both of Sverdlovsk; Evgeny Alexeevich Nechaev, Vologodskoi oblasti, ulitsa Gorkogo, 73, kv. 37; Viktor Petrovich Vinogradov, Vologodskoi oblasti, ulitsa Metallurgoo 10, kv. 21, both of Cherepovets, all of U.S.S.R.

[21] Appl. No.: 493,725

[22] Filed: July 31, 1974

Related U.S. Application Data

[63] Continuation of Ser. No. 302,818, Nov. 1, 1972, abandoned.

[51] Int. Cl.$^2$ ............................................. G01N 27/42
[52] U.S. Cl. .................................. 204/195 S; 264/63; 429/193; 264/66
[58] Field of Search ................ 136/153, 1; 204/195 S; 429/193; 264/63, 66

[56] References Cited

U.S. PATENT DOCUMENTS

| 3,652,427 | 3/1972 | Flood et al. | 204/195 |
|---|---|---|---|
| 3,687,735 | 8/1972 | Inoue | 136/153 |

OTHER PUBLICATIONS

Gulko, Chemical Abstracts, vol. 57, No. 12, 14722(b), Dec. 10, 1962.

*Primary Examiner*—Donald L. Walton
*Attorney, Agent, or Firm*—Haseltine, Lake & Waters

[57] ABSTRACT

Solid electrolyte on the basis of aluminum oxide with the addition of titanium dioxide which further comprises zirconium dioxide.

The components should be used in the following ratio in percent by weight:

| aluminum oxide | 85–95 |
|---|---|
| titanium dioxide | 1–5 |
| zirconium dioxide | 4–10. |

The advantages of the solid electrolyte according to the invention consist in elevated heat and slag resistance. Service life of these solid electrolytes is by at least 3 times longer than that of prior art solid electrolytes.

5 Claims, No Drawings

SOLID METAL OXIDE ELECTROLYTE AND METHOD OF MAKING

This application is a continuation application of Ser. No. 302,818, filed Nov. 1, 1972, now abandoned.

The present invention relates to metallurgical production, and more particularly to solid electrolytes to be used in the metallurgical production for determination of oxidation of molten metals, especially steel in open hearth furnaces and other steel casting installations.

Solid electrolytes are known in the art for determination of oxidation of steel and comprising zirconium dioxide (94%) and calcium oxide (6%) (cf. solid electrolytes disclosed in F.R.G. Pat. Nos. 1,301,917, 1,598,540, 1,300,709 Cl.42 1 or French Pat. Nos. 1,589,710, 1,556,212 Cl. G01 n). In order to produce these electrolytes, starting masses consisting of zirconium dioxide (94%) and calcium oxide (6%) are used.

The disadvantages of the above-mentioned solid electrolytes consist in low heat and slag resistance.

It is known that the service life of these electrolytes in contact with metal and slag does not exceed 20-30 s after which they are completely dissolved. Meanwhile, the service life of solid elecrolytes should be 2-4 hours for continuous operation at temperatures of up to 1680° C.

In order to increase the service life of the electrolytes by protecting them against violent heating, solid electrolytes are covered with protective coatings of diverse composition.

This results in complication of the manufacturing of solid electrolytes and in higher cost of the product not only due to more complicated technological process of manufacuring, but also as a result of the application of protective materials. It should also be noted that the use of protective coatings brings about only slight increases in service life of solid electrolytes.

In addition, such electrolytes do not ensure stable electric properties — nature of conductance. It will be apparent that such electrolytes may be used only for short-term determination of oxidation of metal.

Other known solid electrolytes are made of mullite (synthetic product of the formula 3 $Al_2O_3.2SiO_2$) or spinel (synthetic product of the formula $MgO.Al_2O_3$).

A composition of a starting mass for the production of mullite and spinel electrolytes is identical to the composition of mullite or spinel electrolytes respectively.

Mullite and spinel solid electrolytes, while having somewhat greater heat resistance as compared to zirconium based electrolytes, do not exhibit a suitable slag resistance. In addition, their heat resistance is also insufficient.

Mullite and spinel based products, as well as zirconium electrolytes do not exhibit stable ion conductance response due to decomposition of mullie in the case of mullite based electrolytes and to considerble diffusion of iron into the solid electrolyte in the case of spinel based electrolytes.

Furthermore, in the U.S.S.R. there are known solid electrolytes consisting of magnesium oxide (100 wt.%) or aluminum oxide (99%) with the addition of titanium dioxide (1%).

A composition of a starting mass for the production of magnesium and corundum electrolytes is identical to compositions of the respective electrolytes.

Solid electrolytes of magnesium oxide and aluminum oxide with the addition of titanium dioxide also exhibit low heat resistance.

In addition, the products based on magnesium oxide do not have a constant fraction of ion conductance due to high diffusion of iron into magnesium oxide.

Reliability of operation of magnesium based electrolytes is not more than 30-50% (that is only 30-50 electrolytes operate from every 100) due to low heat resistance. Furthermore, from the very beginning of the determination of oxidation the products lose the nature of conductance due to rapid diffusion of iron into them.

At the same time in the U.S.S.R. there are known solid electrolytes of cast silicon oxide (cast quartz — 100% of $SiO_2$).

A composition of the starting mass of quarts electrolytes is identical to the composition of these electrolytes.

The products made of cast quartz are also hardly suitable for continuous measurement of oxidation of steel due to low slag resistance, as well as due to ready deformation of the products at a temperature as low as 1500° C, since their service life in contact with metal and slag is less than 30-40 minutes at a temperature of up to 1550° C and is much shorter at higher temperatures.

It is the main object of the invention to considerably increase the service life of solid electrolytes (at least up to 2-3 hours), while retaining stable electric characteristids with respect to the ion conductance fraction due to improvement of heat and slag resistance thereof.

It is another object of the invention to increase reliability in operation of solid electrolytes.

Still another object of the inyention is to reduce the cost and to simplify the technological process for the production of solid electrolytes.

The above objects are accomplished according to the invention by further incorporating zirconium dioxide in a solid electrolyte comprising aluminum oxide as the basic component and titanium dioxide, all the above-mentioned components being used in the following ratio in % by weight: aluminum oxide 85-95, zirconium dioxide 4-10, titanium dioxide 1-5.

In accordance with the composition of electrolytes a starting mass to be used in preparation thereof according to the invention is characterized in that, in addition to aluminum oxide and titanium dioxide, it comprises zirconium dioxide, and all the above-mentioned components are used in the following ratio in % by weight: aluminum oxide 85-95, zirconiium dioxide 4-10, titanium dioxide 1-5.

A method of producing the above-described electrolytes according to the invention is characterized in that, in order to mold the products, a starting mass is used which, in addition to aluminum oxide and titanium dioxide, comprises zirconium dioxide introduced therein, aluminum oxide being used in an amount of 85-95%, zirconium dioxide — 4-10% and titanium dioxide — 1-5%.

The advantage of solid electrolytes having the composition according to the invention consists in increased service life in continuous contact with metal of up to 2-4 hours. The reliability of operation of the products (electrolytes) is at least 80-90% (that is 80-90 pieces exhibit stable performance out of every 100), while the reliability of known electrolytes does not exceed 30-50%.

The invention will now be described in more detail with reference to specific examples of embodiments thereof.

The solid electrolyte according to the invention comprises aluminum oxide, zirconium dioxide and titanium dioxide which may be used in the following ratio in percent by weight:

| aluminum oxide | 85-95 |
|---|---|
| zirconium dioxide | 4-10 |
| titanium dioxide | 1-5. |

The solid electrolytes of the above-mentioned composition possess the following properties:

| open porosity | 0-1% |
|---|---|
| apparent density | 3.70-4.1 g/cm³ |
| heat resistance at a temperature of from 1300 to 20° C of a cooling medium (air) | 8-15 cycles |
| fraction of ion conductance | 93-98%. |

The production of solid electrolytes begins with the preparation of a starting mass obtained by mixing finely divided aluminum, zirconium and titanium oxides in amounts corresponding to the composition of the electrolytes, namely:

| aluminum oxide | 85-95% |
|---|---|
| zirconium dioxide | 4-10% |
| titanium dioxide | 1-5%. |

Then paraffin is introduced into the resulting mixture as plasticizer, which is used in an amount of 13-17% by weight based on the dry weight of the oxides mixture. The plasticizer may comprise other products, such as starch, paste and the like approximately in the same amount.

The resulting thermoplastic mass is molded into products in the shape of tubes which are then machined on a lathe to obtain tips.

Then paraffin is extracted until the residue thereof is about 2-3%. This operation is performed by heating molded products (electrolytes) in furnaces up to 200° C in the fill of aluminum oxide. Operational conditions of heating the products for extraction of paraffin are widely known and may be found in the literaure.

Then the products are roasted at 1600°-1650° C in ordinary roasting furnaces. Operational conditions of roasting are also widely known. During this step gradual heating of the products together in a furnace is effected from ambient temperature up to a predetermined temperature, the products are allowed to stay to ensure uniformity of heating and are then cooled together in a furnace to ambient temperature.

The examples illustrating the invention are given herebelow.

EXAMPLE 1

Solid electrolytes in the form of tubular tips of a size of 120×13×8 were prepared which had the following composition in percent by weight:

| aluminum oxide | 94 |
|---|---|
| zirconium dioxide | 4 |
| titanium dioxide | 2. |

The electrolytes exhibited the following properties:

| open porosity | 0.55% |
|---|---|
| apparent density | 3.79 g/cm³ |
| heat resistance at a temperature from 1300 to 20° C of a cooling medium (air) | 10 cycles |
| fraction of ion conductance at 1600° C | 95%. |

A starting mass used to prepare electrolytes was of the composition identical to the composition of the electrolytes both of Example 1 and of the following Examples.

A method of producing solid electrolytes is similar to that above-described both for Example 1 and for other Examples.

EXAMPLE 2

Solid electrolytes in the shape of tubular tips of a size of 120×13×8 were prepared which had the following composition in percent by weight:

| aluminum oxide | 93 |
|---|---|
| zirconium dioxide | 5 |
| titanium dioxide | 2. |

The electrolytes exhibited the following properties:

| open porosity | 0.40% |
|---|---|
| apparent density | 3.81 g/cm³ |
| heat resistance at a temperature from 1300 to 20° C of a cooling medium (air) | 11 cycles |
| fraction of ion conductance at 1600° C | 95.5%. |

EXAMPLE 3

Solid electrolytes in the shape of tubular tips of a size of 120×13×8 were made which had the following composition in percent by weight:

| aluminum oxide | 93 |
|---|---|
| zirconium dioxide | 4 |
| titanium dioxide | 3. |

The electrolytes exhibited the following

| open porosity | 0.80% |
|---|---|
| apparent density | 3.80 g/cm³ |
| heat resistance at a temperature from 1300 to 20° C of a cooling medium (air) | 10 cycles |
| fraction of ion conductance at 1600° C | 95.0%. |

EXAMPLE 4

Solid electrolytes in the shape of tubular tips of a size of 120×13×8 were made which had the following composition in percent by weight:

| aluminum oxide | 86 |
|---|---|
| zirconium dioxide | 10 |
| titanium dioxide | 4. |

The electrolytes exhibited the following properties:

| | |
|---|---|
| open porosity | 0.06% |
| apparent density | 4.03 g/cm³ |
| heat resistance at a temperature from 1300 to 20° C of a cooling medium (air) | 14 cycles |
| fraction of ion conductance at 1600° C | 97%. |

EXAMPLE 5

Solid electrolytes in the shape of tubular tips of a size of 120×13×8 were made which had the following composition in percent by weight:

| | |
|---|---|
| aluminum oxide | 87 |
| zirconium dioxide | 10 |
| titanium dioxide | 3. |

The electrolytes exhibited the following properties:

| | |
|---|---|
| open porosity | 0.88% |
| apparent density | 4.10 g/cm³ |
| heat resistance at a temperature from 1300 to 20° C of a cooling medium (air) | 10 cycles |
| fraction of ion conductance at 1600° C | 97%. |

What is claimed is:

1. A method for producing a solid electrolyte suitable for use in determining oxidation of molten metals and consisting essentially of aluminum oxide, titanium dioxide and zirconium oxide comprising the steps of
   mixing 85–95 weight % aluminum oxide, 1–5 weight % of titanium dioxide and 4–10 weight % of zirconium dioxide, the percentages of said oxides adding up to 100%;
   adding a plasticizer to said mixture;
   molding an article from the plasticized mixture;
   drying the molded article; and
   roasting the dried article.

2. A method according to claim 1 wherein said oxides are mixed in finely divided form.

3. A method according to claim 1 wherein the plasticizer is selected from the group consisting of paraffin and starch paste.

4. A method according to claim 1 wherein the roasting step is carried out at 1600°–1650° C.

5. The product obtained by the method of claim 1 having an open porosity of 0–1%, an apparent density of 3.70–4.1 g/cm³, a heat resistance of 8–15 cycles from 1300 to 20° C. and an ion conductance of 93–98%.

* * * * *